(12) United States Patent
Roberts

(10) Patent No.: US 11,166,626 B2
(45) Date of Patent: Nov. 9, 2021

(54) CAP AND TUBE SET FOR USE IN A MEDICAL PROCEDURE

(71) Applicant: KEYMED (MEDICAL & INDUSTRIAL EQUIPMENT) LTD., Essex (GB)

(72) Inventor: Tim Roberts, Essex (GB)

(73) Assignee: KEYMED (MEDICAL & INDUSTRIAL EQUIPMENT) LTD.

(*) Notice: Subject to any disclaimer, the term of this patent is extended or adjusted under 35 U.S.C. 154(b) by 82 days.

(21) Appl. No.: 16/085,637

(22) PCT Filed: Mar. 27, 2017

(86) PCT No.: PCT/GB2017/050854
§ 371 (c)(1),
(2) Date: Sep. 17, 2018

(87) PCT Pub. No.: WO2017/168134
PCT Pub. Date: Oct. 5, 2017

(65) Prior Publication Data
US 2019/0090725 A1 Mar. 28, 2019

(30) Foreign Application Priority Data
Mar. 31, 2016 (GB) .................................... 1605416

(51) Int. Cl.
*A61B 1/00* (2006.01)
*B65D 43/08* (2006.01)
*A45F 3/16* (2006.01)

(52) U.S. Cl.
CPC .............. *A61B 1/00137* (2013.01); *A45F 3/16* (2013.01); *A61B 1/00128* (2013.01); *B65D 43/08* (2013.01); *A61B 1/00119* (2013.01)

(58) Field of Classification Search
CPC ............ A61B 1/00137; A61B 1/00128; A61B 1/00119; B65D 43/08; A45F 3/16
(Continued)

(56) References Cited

U.S. PATENT DOCUMENTS 2,665,816 A * 1/1954 Anft ..................... B65D 1/04
220/524
3,269,389 A * 8/1966 Meurer ............... B05B 11/0078
128/200.14

(Continued)

FOREIGN PATENT DOCUMENTS

CN 202743709 U 2/2013
WO 2011060192 A1 5/2011

OTHER PUBLICATIONS

Authorized Officer Martin Fischer, date of mailing Sep. 27, 2017, PCT/GB2017/050854,International Search Report (PCT Article 18 and Rules 43 and 44).

(Continued)

*Primary Examiner* — J. Gregory Pickett
*Assistant Examiner* — Niki M Eloshway
(74) *Attorney, Agent, or Firm* — Luedeka Neely Group, PC

(57) ABSTRACT

A cap for a container comprises an annular collar with a longitudinal axis and a diameter perpendicular thereto. A seal includes two seal elements which cooperate to form a generally cylindrical seal member locatable in the collar with the seal elements in contact with each other in a plane parallel to the longitudinal axis. At least one of the seal elements has at least one opening therethrough. The openings are configured to receive the tubes of a medical tube set and the cap can be constructed with different combinations of seal members to provide a different number of openings into the container.

12 Claims, 5 Drawing Sheets

(58) Field of Classification Search
USPC ............ 215/6; 220/341, 523, 524, 526, 253, 220/254.2, 319
See application file for complete search history.

(56) References Cited

U.S. PATENT DOCUMENTS

| | | | | |
|---|---|---|---|---|
| 3,693,847 | A * | 9/1972 | Gibson | B65D 47/122 |
| | | | | 222/546 |
| 5,143,261 | A * | 9/1992 | Drobish | B65D 81/3216 |
| | | | | 222/129 |
| 5,573,143 | A * | 11/1996 | Deardurff | B29C 45/26 |
| | | | | 222/129 |
| 5,765,725 | A * | 6/1998 | Matt | B65D 35/22 |
| | | | | 222/129 |
| 6,254,529 | B1 | 7/2001 | Ouchi | |
| 7,090,072 | B1 * | 8/2006 | Elliott | B44D 3/122 |
| | | | | 206/15.3 |
| 8,123,057 | B2 * | 2/2012 | Kunz | B65D 50/046 |
| | | | | 215/216 |
| 2003/0173364 | A1 * | 9/2003 | Eva | B65D 25/2894 |
| | | | | 220/524 |
| 2007/0235105 | A1 | 10/2007 | Ramsey et al. | |
| 2012/0226104 | A1 * | 9/2012 | Ikeda | A61B 1/0669 |
| | | | | 600/129 |
| 2014/0326731 | A1 * | 11/2014 | Raymus | A47G 19/2272 |
| | | | | 220/524 |
| 2015/0021288 | A1 * | 1/2015 | Eckhoff | A61J 1/1406 |
| | | | | 215/6 |
| 2015/0296063 | A1 | 10/2015 | Reeves | |
| 2018/0264494 | A1 * | 9/2018 | Yamamoto | B05B 11/0086 |

OTHER PUBLICATIONS

Authorized Officer Martin Fischer, Written Opinion of the International Searching Authority (PCT Rule 43bis.1), PCT/GB2017/050854; no date available.

Examiner Tom Harris, Patents Act 1977: Search Report under Section 17, GB1605416.5 Date of Search Aug. 31, 2016.

Applicant Yoshida Kogyo Co., Ltd. The Lid of The Bottle Container, filed 1975, Japan, JP11976148336.

Yusuke Terauchi, A Sealed Container, Date of Publication Nov. 1, 1989, JP11989158461.

* cited by examiner

Section A-A

CAP AND TUBE SET FOR USE IN A MEDICAL PROCEDURE

CROSS-REFERENCE TO RELATED APPLICATION

This application claims priority under all applicable statutes and is a U.S. National phase (37 U.S.C. Section 371) of International Application PCT/GB2017/050854, filed Mar. 27, 2017, and entitled CAP AND TUBE SET FOR USE IN A MEDICAL PROCEDURE, which claims priority to GB 1605416.5, filed Mar. 31, 2016, incorporated herein by reference in their entireties.

The present invention relates to a cap for use with a container and tubing set in a medical procedure such as an endoscopy. Specifically, the present invention provides a configurable cap and seal system with a modular seal which can be assembled in different combinations to suit the form of tube set being used in a particular procedure, and a tube set incorporating the cap.

When carrying out an endoscopy, it is usual to provide a supply of liquid, such as water, and a supply of gas, such as $CO_2$, to an endoscope. Water or other liquid may be used to clean the lens at the distal end of the endoscope and to irrigate or flush the site being viewed to clean away debris. Gas may be supplied to insufflate the body cavity under inspection. In many existing systems, two separate water bottles are provided, one bottle providing water for lens cleaning and the other providing water for flushing. In each case, a tube for carrying the water may pass through a cap fitted to the water bottle and have its free end below the surface of the water. The other end of the tube will be connected to the endoscope. Insufflation gas may be supplied through a second tube into one bottle to fill the space above the water. A third tube may then be provided to take the insufflation gas from the bottle to the endoscope.

Thus, users need to prepare two water bottles, with replacements/refills available as necessary, and tube sets must be connected to each bottle as required. In addition, different bottle caps are required to suit different tube sets. This increases the complexity of the system and the set-up time required and may also delay the procedure if bottles need to be changed partway through.

The present invention provides a cap for a container, comprising an annular collar with a longitudinal axis and a diameter perpendicular thereto, and a seal comprising two seal elements which co-operate to form a generally cylindrical seal member locatable in the collar with the seal elements in contact with each other in a plane parallel to the longitudinal axis, wherein at least one seal element comprises at least one opening therethrough.

In this way, a cap can be constructed using different combinations of seal elements to suit different tube sets. It is also possible to use the cap with a single water bottle providing water and gas for all the requirements needed in the endoscopy procedure, to avoid the need for two separate bottles and tube sets.

In one embodiment, both seal elements comprise at least one opening therethrough.

Preferably, each seal element is generally semi-cylindrical.

The collar may comprise a side wall with upper and lower ends and an annular flange projecting inwardly from the side wall at the upper end. A thread may be formed on an interior surface of the collar for engagement with a corresponding thread on a container.

Each seal element may comprise a recess in a lower surface to receive a rim of a container. The seal elements may seal against an interior surface of the collar.

The present invention also provides a kit for forming a cap for a container as described above, the kit comprising an annular collar and at least three seal elements, wherein any two of the seal elements are combinable to create a seal member locatable in the collar.

Preferably, in the kit, at least one seal element has no openings therethrough, at least one seal element has one opening therethrough, and at least one seal element has more than one opening therethrough.

The present invention also provides tube set comprising a cap for a container as described above, wherein each seal element comprises two openings, and a tube is fitted through each of the openings.

This provides a hybrid tube set with four tubes which can be used for gas or liquid supply as required.

In particular, in one embodiment, first and second tubes are adapted to supply liquid from a container to which the cap is connected to a medical instrument. A third tube may be adapted to pass gas between a container to which the cap is connected and a medical instrument. A fourth tube may be adapted to supply gas from an external source into a container to which the cap is connected.

The invention will now be described in detail, by way of example only, with reference to the accompanying drawings, in which:—

Figure 1:
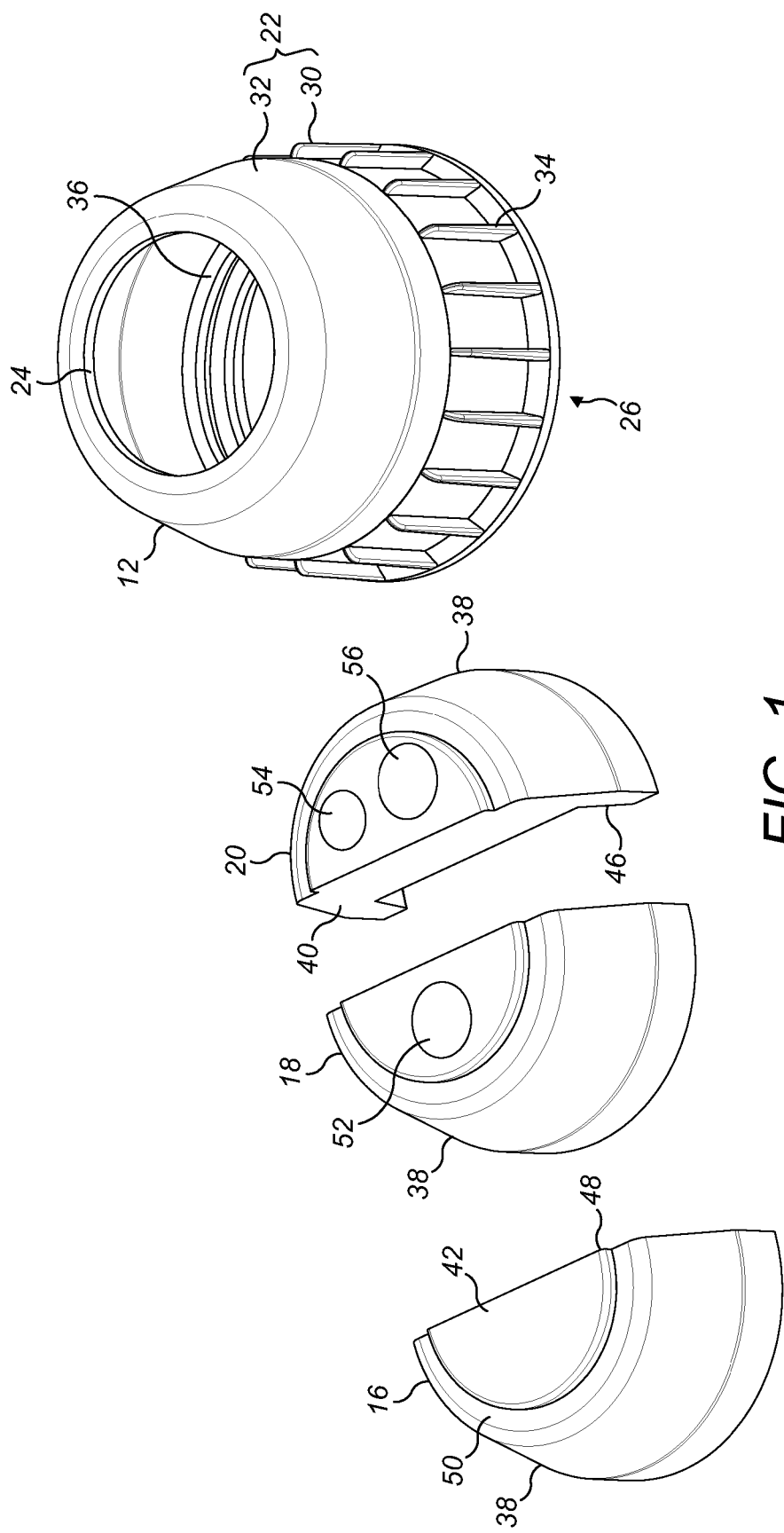
FIG. 1 is an exploded perspective view of the components of the cap in accordance with one embodiment of the present invention.

With reference to FIGS. 1-7, a bottle cap 10 in accordance with one embodiment of the present invention comprises a collar 12 with a modular seal 14. Three forms of seal element 16, 18, 20 are provided and any two forms of seal element at a time can be combined to create the modular seal 14 for fitting within the collar 12 to form an assembled cap 10.

The collar 12 is typically formed of plastic and consists of a generally annular side wall 22 with open upper and lower ends 24, 26. The collar 12 has a longitudinal axis X (best seen in FIG. 7) and a diameter perpendicular to the axis (corresponding to the section line AA seen in FIG. 6). An annular flange 28 extends inwardly from the side wall 22, to surround the opening at the upper end 24. In this example, the side wall 22 comprises a generally cylindrical lower portion 30 and a frusto-conical upper portion 32. The exterior of the side wall 22, particularly on the cylindrical lower portion 30, may be formed with ribs 34 or other surface formations for enhanced grip when a user is fitting the cap 10 to a bottle. The interior of the side wall 20, particularly on the cylindrical lower portion 30, is formed with a thread 36 to engage a thread on the neck of a plastic water bottle. The thread 36 is preferably formed with a relatively large pitch and relatively deep threads so that it is capable of fitting on a number of different bottle or container necks which have different dimensions.

Each seal element 16, 18, 20 comprises a block of elastomeric material which is generally semi-cylindrical in shape. Any two seal elements can be combined to form a generally cylindrical seal 14 which fits within the collar 12. Thus, each seal element 16, 18, 20 has a generally semi-cylindrical side surface 38 and a planar face 40, with generally semi-circular upper and lower surfaces 42, 44. The seal elements 16, 18, 20 are shaped and dimensioned to fit within the collar 12 and thus, in this example, the side surface 38 may have an upper portion which is part of a frusto-conical surface, and a lower portion which is semi-cylindrical.

The lower surface 44 of each seal element may include a semi-circular recess 46 which receives the upper rim of a bottle neck in use.

The upper surface 42 of each seal element 16, 18, 20 includes a raised semi-circular plateau 48 with an arcuate surface 50 around it.

One form of seal element 16 is provided as a solid body of elastomeric material. A second form of seal element 18 is formed with a cylindrical opening 52, extending through the body from top to bottom. It may be generally centrally placed in the raised plateau 46. A third form of seal element 20 may be formed with two cylindrical openings 54, 56 extending through the seal element from top to bottom. Preferably, one opening 54 has a smaller diameter than the other opening 56.

The openings 52, 54, 56 are sized to receive tubes of a tubing set as described further below.

Figure 7:
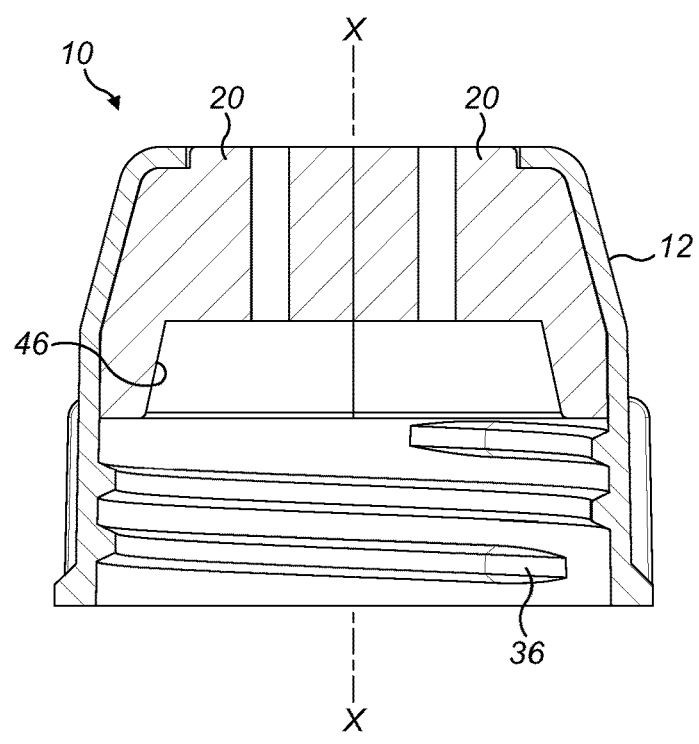
FIG. 7 shows a cross-section of the cap of FIGS. 5 and 6 along the line AA.

In use, any two seal elements 16, 18, 20 can be placed with their planar faces 40 in contact with each other to form a generally cylindrical seal member 14, which is then received within the collar 12. Thus, the pair of seal elements contact each other in a plane which is parallel to the longitudinal axis of the collar 12. The planar faces 40 lie generally on a diameter of the collar 12. The seal elements are dimensioned to form a tight fit and to seal against each other and against the inner surfaces of the collar 12 with no gaps (as seen in FIG. 7). The lower surface of the annular flange 28 on the collar 12 contacts the arcuate surface 50 surrounding the raised plateau 46 of the seal elements. The side surfaces 38 of the seal elements seal against interior surfaces of the collar 12, and in particular the frusto-conical portions of the seal elements seal against the frusto-conical portion 32 of the collar 12. The combined collar 12 and chosen pair of seal elements thus create a cap 10 which can then be fitted on to the neck of a bottle.

The faces 40 of the seal elements which fit together are illustrated as flat surfaces. However, each seal element 16, 18, 20 could be formed with features to co-operate and key two seal elements together. For example, each could include a projection and a recess in face 40, so that two seal elements can be keyed together in order to facilitate fitting the combined seal 14 into the collar 12 in order to assemble the cap 10.

Figure 2:
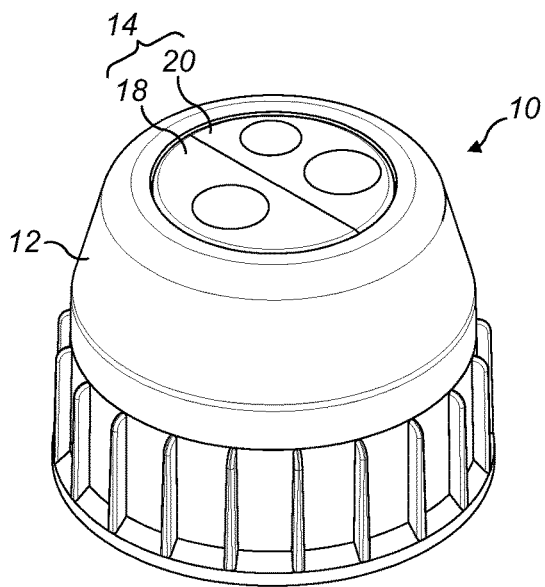
FIG. 2 shows the assembled cap in a first possible configuration.

One possible configuration of cap 10, as shown in FIG. 2, includes seal elements 18 and 20 so that a total of three openings are provided through the seal member 14. This configuration can be used in a hybrid system which has a single water bottle. The smaller opening 54 in seal element 20 may receive a tube supplying gas such as $CO_2$ into the bottle. The larger opening 56 receives a co-axial tube consisting of an outer tube and an inner tube, which extends beyond the end of the outer tube. The longer inner tube extends into the water in the bottle and water can be passed through this tube to the endoscope for lens cleaning purposes. The end of the outer tube is above the water level and can therefore pass gas in the top of the bottle to the endoscope for insufflation. The opening 52 in the seal element 18 receives another tube which extends into the water in the bottle and provides water to the endoscope for irrigation purposes.

Figure 3:
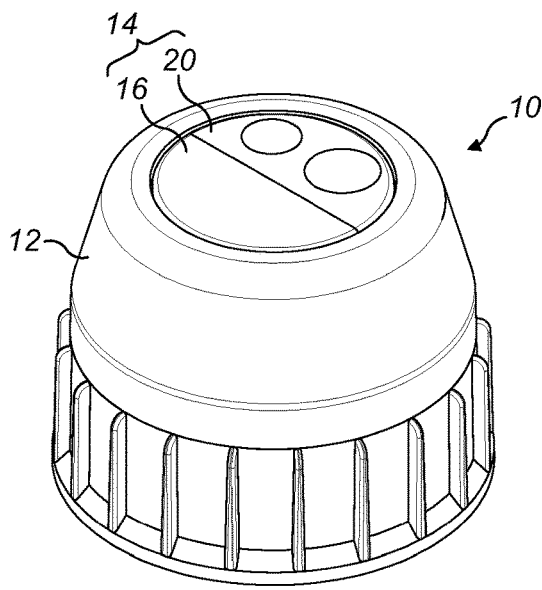
FIG. 3 shows the assembled cap in a second possible configuration.

FIG. 3 shows a second possible configuration which uses seal elements 16 and 20, providing two openings 54, 56. The smaller opening 54 receives a gas supply tube for passing gas into the bottle. The larger opening 56 receives a co-axial tube as described above for passing both water and gas from the bottle to the endoscope.

Figure 4:
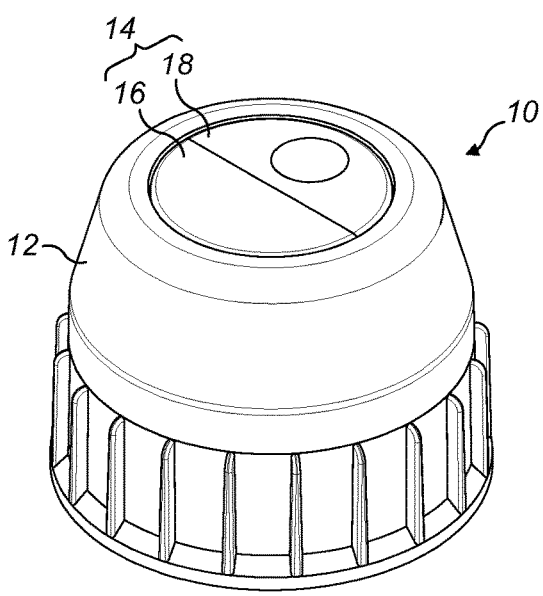
FIG. 4 shows the assembled cap in a third possible configuration.

FIG. 4 shows a third possible configuration using seal elements 16 and 18. This provides a single opening through the cap 10. This may receive a co-axial air and water tube. In this case, air enters the bottle via the outer tube and water exits the bottle via the inner tube.

Figure 5:
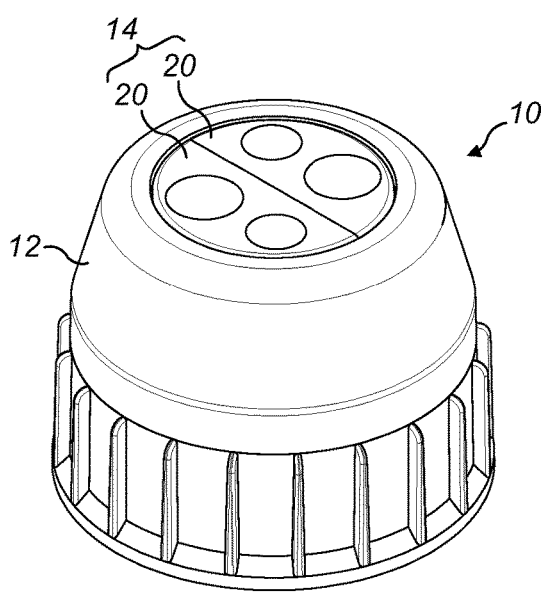
FIG. 5 shows the assembled cap in a fourth possible configuration.
Figure 6:
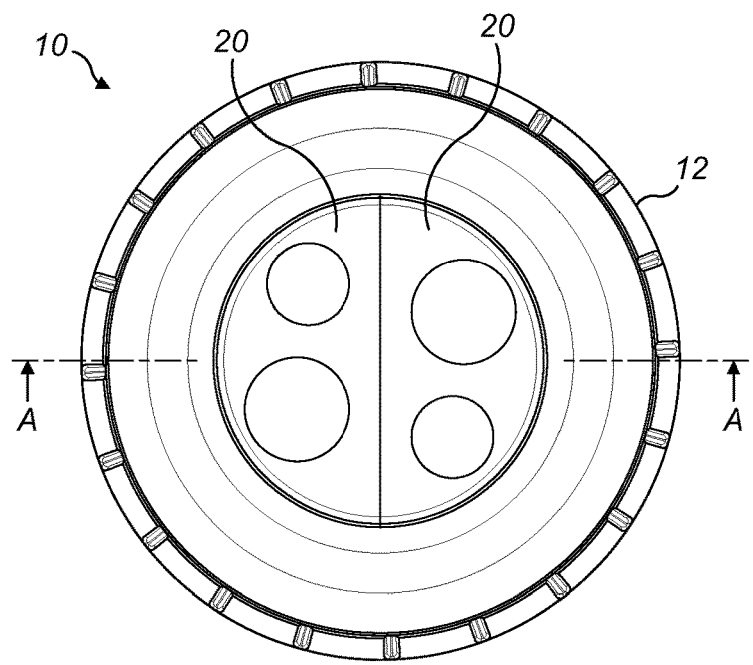
FIG. 6 shows a top view of the cap of FIG. 5.

FIGS. 5-7 show a fourth possible configuration of cap 10 using two seal elements 20, thus providing four openings through the cap 10.

Figure 8:
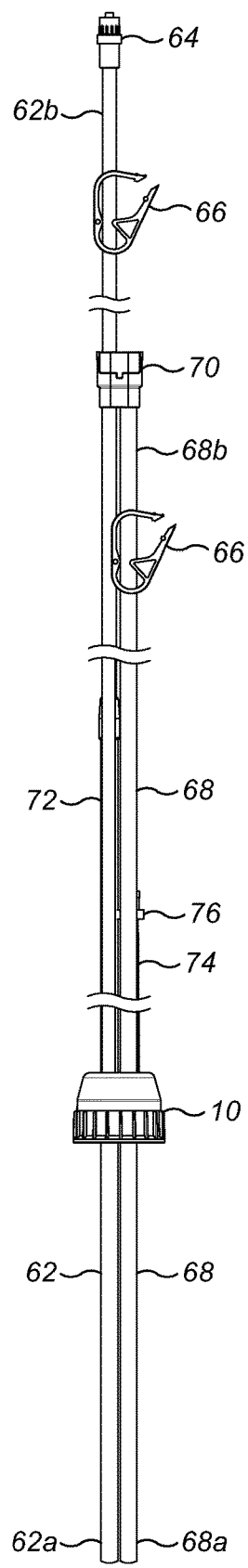
FIG. 8 is a front view of a tube set incorporating the cap of FIGS. 5-7.
Figure 9:
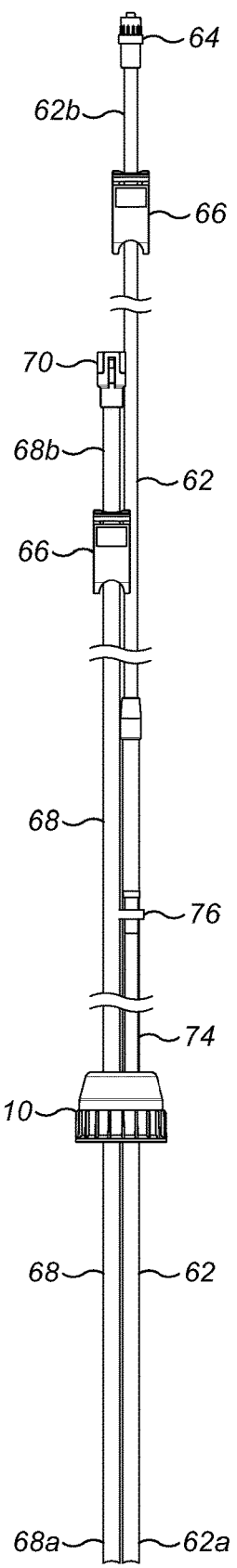
FIG. 9 is a side view of the tube set of FIG. 8.

FIGS. 8 and 9 illustrate a tube set 60 which incorporates this fourth configuration of cap 10 and has four tubes 62, 68, 72, 74 fitted through the seal 14 in the cap 10.

Figure 10:
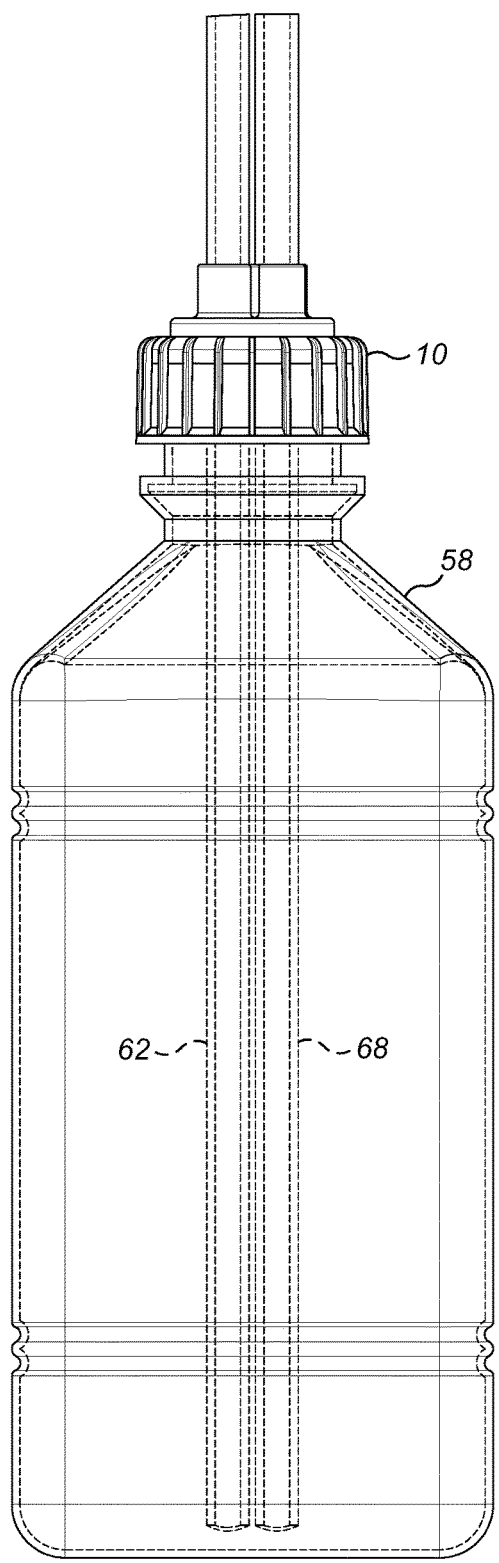
FIG. 10 is a side view of part of the tube set of FIGS. 8 and 9 connected to a bottle.

FIG. 10 shows the cap 10 and parts of the tubes when connected to a typical water bottle 58.

In this example, the first tube 62 comprises an irrigation tube 62 which is used to pass water (or other liquid) from a bottle to which the cap 10 is connected to an endoscope, to irrigate a site under observation. The proximal end 62a of the irrigation tube 62 passes through the cap 10 and is dimensioned to extend well into a bottle so that it will be close to the bottom surface of the bottle when the cap 10 is secured to the neck. The distal end 62b of the irrigation tube 62 includes a connector 64 for connecting the irrigation tube 62 to an endoscope. Typically, the connector 64 will include a one-way valve to prevent backflow of liquid from the endoscope into the tube 62. Usually, the irrigation tube 62 will be provided with a conventional clamp 66. This is illustrated in the open position, but in the closed position, this squeezes the tube 62 to close it, to prevent leakage when it is disconnected from an endoscope.

The second tube 68 comprises a rinsing tube 68 which is used to pass water (or other liquid) from a bottle to which the cap 10 is connected to an endoscope to rinse the lens and prevent the view being obscured. As with the irrigation tube 62, the rinsing tube 68 includes a proximal end 68a extending well into the bottle so that in use it will be close to the bottom surface. The distal end 68b includes a connector 70 for connection to an endoscope. As described below, the connector 70 may be common with a connector at the end of a third tube 72. The rinsing tube 68 may also be fitted with a clamp 66 to close off the tube 68 when it is disconnected from an endoscope to prevent leakage.

The third tube is a gas tube 72 (also commonly referred to as an air tube) which is used to supply air (or other gas) from a bottle to which the cap 10 is connected to an endoscope. The proximal end 72a terminates just below the seal 14 in the cap 10 so that it is well above the level of water in the container. The distal end 72b includes a connector for connection to the endoscope and, as noted above and illustrated in FIGS. 8 and 9, this may be combined with the connector 70 for the rinsing tube 68.

A fourth tube 74 is a gas supply tube, for example, for supply $CO_2$ into the bottle. The proximal end 74a terminates just beneath the seal 14 and well above the level of any water in the container. The distal end 74b has a connector 76 including a check valve, for connection to an external gas supply.

In use, the tube set 60 is connected to a bottle or other container by screwing the cap 10 onto the bottle neck. The irrigation and rinsing tubes 62, 68 extend into the liquid within the bottle. If an external gas supply is used, gas is passed into the bottle to fill the space above the water. The gas pressurises the bottle to help water flow through the irrigation and rinsing tubes 62, 68. Gas may also be passed from the bottle through the gas tube 72 to the endoscope for insufflation purposes.

The tube set 60 can also be used without the external gas supply. In this case, the gas supply tube 74 is not used and is closed by virtue of the check valve in the connector at its distal end 74b. In this case, compressed air (or other gas) is normally supplied separately to the endoscope and the endoscope includes a control button which, when pressed by a user directs air from the separate supply for the endoscope back into the bottle via the gas tube 72. This pressurises the bottle to force water through the rinsing tube 68.

In this way, the tube set 60 provides a hybrid system which can be used with a single water bottle to supply both irrigation and rinsing liquid to an endoscope and it can be used either with a gas supply from an external source for insufflation or can be used to utilise air otherwise supplied to the endoscope.

The configurations of cap and tube set described above are likely to be the most common combinations, but it will be appreciated that other configurations are possible. For example, in the cap 10, two solid seal elements 16 could be provided when it is simply desired to close off the water bottle and prevent leakage of any water remaining inside. Alternatively, two seal elements 18 could be provided to give two openings of the same diameter. Thus, any combination of the different seal elements can be provided as desired to suit the number of tubes required.

A cap 10 in accordance with the present invention may be provided in kit form so that a user can select the appropriate configuration required. For example, the kit may consist of all the components shown in FIG. 1, that is, one each of seal elements 16, 18, 20 and one collar 12. Alternatively, multiples of the different seal elements could be provided to accommodate further combinations.

In this way, a hospital need only stock one type of kit which will provide options for different configurations of bottle cap 10 to suit a desired application. The user can select the appropriate seal elements to form a desired bottle cap and this, in turn, will alleviate the need for two separate water bottles in a procedure.

Similarly, a hospital may stock the assembled hybrid tube set 60 as described above which can be used as desired, making use of all four tubes or with unused tubes closed by the clamps 66 or by virtue of the check valves in the relevant connectors.

The components of the cap 10 and tube set 60 may be simple plastic mouldings designed for single use and then disposal, or they may be formed of materials which can be suitably cleaned and sterilised for re-use.

The invention claimed is:

1. A cap for a container having an annular open neck, the cap comprising an annular collar with a longitudinal axis and a diameter perpendicular thereto, a side wall with open upper and lower ends and an annular flange projecting inwardly from the side wall at the upper end, and a seal comprising two seal elements which co-operate to form a generally cylindrical seal member, the seal elements each provided by a block of elastomeric material shaped and dimensioned to fit side by side within the annular collar to form a tight fit and to contact and seal against each other and against inner surfaces of the collar with no gaps to provide the cap which can be fitted onto the open neck of the container, with the seal elements in contact with each other in a plane parallel to the longitudinal axis and an upper surface of each seal element is exposed in the upper open end of the collar, and wherein at least one seal element comprises at least one opening therethrough.

2. A cap as claimed in claim 1, wherein both seal elements comprise at least one opening therethrough.

3. A cap as claimed in claim 1, wherein each seal element is generally semi-cylindrical.

4. A cap as claimed in claim 1, wherein a thread is formed on an interior surface of the collar for engagement with a corresponding thread on a container.

5. A cap as claimed in claim 1, wherein each seal element comprises a recess in a lower surface to receive a rim of a container.

6. A cap as claimed in claim 1, wherein the seal elements seal against an interior surface of the collar.

7. A kit for forming a cap for a container as claimed in claim 1, the kit comprising an annular collar and at least three seal elements, wherein any two of the seal elements are combinable to create a seal member locatable in the collar.

8. A kit as claimed in claim 7, wherein at least one seal element has no openings therethrough, at least one seal element has one opening therethrough, and at least one seal element has more than one opening therethrough.

9. A tube set comprising a cap as claimed in claim 1, wherein each seal element comprises two openings, and a tube fitted through each opening with a tube fitted through each opening in sealing engagement therewith.

10. A tube set as claimed in claim 9, wherein first and second tubes are adapted to supply liquid from a container to which the cap is connected to a medical instrument.

11. A tube set as claimed in claim 10, wherein a third tube is adapted to pass gas between a container to which the cap is connected and a medical instrument.

12. A tube set as claimed in claim 11, wherein a fourth tube is adapted to supply gas from an external source into a container to which the cap is connected.

* * * * *